US006156775A

United States Patent [19]
Schmutz

[11] Patent Number: 6,156,775
[45] Date of Patent: Dec. 5, 2000

[54] USE OF FLUORINATED TRIAZOLES IN TREATING AFFECTIVE AND ATTENTION DISORDERS

[75] Inventor: Markus Schmutz, Schoenenbuch, Switzerland

[73] Assignee: Novartis AG, Basel, Switzerland

[21] Appl. No.: 09/259,910

[22] Filed: Mar. 1, 1999

[51] Int. Cl.[7] .................................................. A61K 31/415
[52] U.S. Cl. ............................................................ 514/359
[58] Field of Search ................................................ 514/359

[56] References Cited

U.S. PATENT DOCUMENTS

| | | | |
|---|---|---|---|
| 4,966,909 | 10/1990 | Kane etal. | 514/359 |
| 4,977,145 | 12/1990 | Sudilovsky | 514/91 |
| 5,747,515 | 5/1998 | Boar et al. | 514/359 |

*Primary Examiner*—James H. Reamer
*Attorney, Agent, or Firm*—Joseph J. Borovian

[57] ABSTRACT

The present invention relates to the use of fluorinated triazoles in treating affective disorders.

8 Claims, No Drawings

USE OF FLUORINATED TRIAZOLES IN TREATING AFFECTIVE AND ATTENTION DISORDERS

The present invention relates to a new pharmaceutical use of fluorinated triazoles.

More particularly the present invention relates to a new pharmaceutical use for compounds of formula I

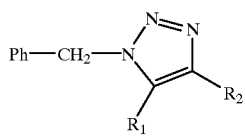

(I)

wherein Ph is an o-fluorinated phenyl radical which may be additionally substituted by 1 or 2 halogen atoms selected from fluorine and chlorine, $R_1$ is hydrogen, carbamoyl, N-$(C_2-C_5)$alkanoylcarbamoyl or N,N-di$(C_1-C_4)$ alkylcarbamoyl, and $R_2$ is carbamoyl, N-$(C_2-C_5)$ alkanoylcarbamoyl or N,N-di$(C_1-C_4)$alkylcarbamoyl.

The compounds of formula I as well as their production process are known e.g. from European Patent No. 199 262. This patent also discloses the use of the compounds of formula I for the treatment of convulsions of different origin, e.g. of epilepsy.

In accordance with the present invention, it has now surprisingly been found that the compounds of formula I are useful in the treatment of affective disorders including bipolar mood disorders.

The activity of the compounds of formula I in said treatment is evidenced, for example, in the following tests suitable for detecting drugs having potential behavioral desinhibitory and/or sociotropic effects which are thought to be relevant for recovery from social withdrawal, a cardinal feature of depression and related psychiatric conditions.

a) The half enclosed platform test

This test is basically as described in Psychopharmacology, 1986, 89:31–37.

Groups of 12 male OF-1 mice are given vehicle or the substance 1 hour before being tested on the platform. The apparatus consists of a transparent platform perforated with 25 equally-spaced 1 cm holes. The platform is divided into equal halves by a 15 cm high, semi-rectangular wall enclosing one half of the platform, the other half having open edges. The whole platform rests on four 15 cm high legs. A line down the middle runs from the edge of one wall to the edge of the opposite wall. The experiment consists of placing a mouse on the midline and recording their behavior for 5 minutes as they explore the platform. In particular, the mean frequencies and durations of the behavioral elements are recorded and statistical comparisons are determined using the Kruskal-Wallis "H" test followed by paired comparisons between control and treatment groups using the Mann-Whitney U-test. Probabilities (p=/<0.05) quoted are 2-tailed.

At doses of about 0.3 to about 10 mg/kg p.o., the compounds of formula I significantly increase exploratory behavior, such as stretched attend posture, head raising and forward locomotion, in the open half of the platform, which decreasing the frequency of stationary elements, such as sitting still and inactivity, in the enclosed half of the platform.

b) The intruder mouse test

This test is basically as described in Triangle, 1982, 21:95–105 and J. Clin. Psychiatry, 1994, 55:9 (suppl. B) 4–7.

A grouped "intruder" mouse is given the substance or the vehicle route 1 hour before being confronted for 6 minutes with an untreated isolated, aggressive mouse (resident) in a neutral cage. Each group consisted of 8 mice. The social encounter is videotaped and an observer records occurrence and duration of over 60 behavioral elements covering the non-social and social forms of the animals' behavioral repertoire. Frequency, duration and, when required, the sequence of the elements are recorded. The median frequencies and durations of the behavioral elements are recorded for each category and statistical comparisons are determined using the Kruskal-Wallis "H" test followed by paired comparisons between control and treatment groups using the Mann-Whitney "U" test. Probabilities (p=/<0.05) quoted are 2-tailed.

At doses of about 1 to about 10 mg/kg p.o., the compounds of formula I significantly increase non-social behavior and social investigation in the treated intruder mouse, while reducing defensive ambivalence, arrested flight and escape.

In view of their behavioral desinhibitory (=anxiolytic-/antidepressant-like) and sociotropic activity, the compounds of formula I are useful in the treatment of affective disorders including bipolar disorders, e.g. manic-depressive psychoses, extreme psychotic states e.g. mania, schizophrenia, and excessive mood swings where behavioral stabilization is desired. In addition, the compounds are indicated in ADHD (attention deficit hyperactivity disorders) and other attention disorders, e.g. autism, anxiety states, generalized anxiety and agoraphobia, as well as those behavioral states characterized by social withdrawal e.g. negative symptoms.

In a preferred group of formula I for use according to the invention, Ph is o-fluorophenyl, 2,5-difluorophenyl, 2,6-difluorophenyl or 2-chloro-6-fluorophenyl, $R_2$ is hydrogen or carbamoyl and $R_2$ is carbamoyl. The compound 1-(2,6-difluorophenyl)methyl-1H-1,2,3-triazole-4-carboxamide is particularly preferred.

For the above-mentioned indications the appropriate dosage will of course vary depending upon, for example, the compound employed, the host, the mode of administration and the nature and severity of the condition being treated. However, in general, satisfactory results in animals are indicated to be obtained at a daily dosage of from about 1 to about 50 mg/kg animal body weight. In larger mammals, for example humans, an indicated daily dosage is in the range from about 50 to about 3500 mg of a compound according to the invention conveniently administered, for example, in divided doses up to four times a day.

The compounds of formula I may be administered in any usual manner, e.g. orally, for example in the form of tablets or capsules, or parenterally, for example in the form of injection solutions or suspensions.

The present invention also provides pharmaceutical compositions comprising a compound of formula I in association with at least one pharmaceutical carrier or diluent, for use in the treatment of neuropathic pain. Such compositions may be manufactured in conventional manner. Unit dosage forms may contain for example from about 10 mg to about 1500 mg of the compound of formula I.

For example tablets each containing 50 mg, or film-coated tablets each containing 100 mg, of 1-(2,6-difluorophenyl) methyl-1H-1,2,3-triazole-4-carboxamide, may be prepared as described in Examples 15 and 16 of EP 199262.

The invention further provides the use of a compound of formula I for the manufacture of a pharmaceutical composition for the treatment of affective disorders.

The invention furthermore provides a method for the treatment of affective disorders in a subject in need of such treatment, which comprises administering to said subject a therapeutically effective amount of a compound of formula I.

What is claimed is:

1. A method for treating affective disorders which comprises administering to a subject in need of such treatment a therapeutically effective amount of a compound of formula I

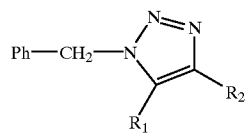

(I)

wherein

Ph is o-fluorophenyl or o-fluorophenyl independently mono- or di-substituted by fluoro or chloro;

$R_1$ is hydrogen, carbamoyl, $N\text{-}(C_2\text{-}C_5)$ alkanoylcarbamoyl or $N,N\text{-}di(C_1\text{-}C_4)$alkylcarbamoyl; and $R_2$ is carbamoyl, $N\text{-}(C_2\text{-}C_5)$alkanoylcarbamoyl or $N,N\text{-}di(C_1\text{-}C_4)$alkylcarbamoyl.

2. A method according to claim 1 wherein the compound administered is 1-(2,6-difluorophenyl)methyl-1H-1,2,3-triazole-4-carboxamide.

3. A method according to claim 1 wherein the affective disorder is bipolar mood disorder.

4. A method according to claim 3 wherein the compound administered is 1-(2,6-difluorophenyl)methyl-1H-1,2,3-triazole-4-carboxamide.

5. A method for treating attention disorders which comprises administering to a subject in need of such treatment a therapeutically effective amount of a compound of formula I

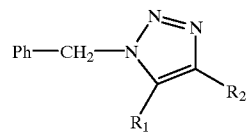

(I)

wherein

Ph is o-fluorophenyl or o-fluorophenyl independently mono- or di-substituted by fluoro or chloro;

$R_1$ is hydrogen, carbamoyl, $N\text{-}(C_2\text{-}C_5)$ alkanoylcarbamoyl or $N,N\text{-}di(C_1\text{-}C_4)$alkylcarbamoyl; and $R_2$ is carbamoyl, $N\text{-}(C_2\text{-}C_5)$alkanoylcarbamoyl or $N,N\text{-}di(C_1\text{-}C_4)$alkylcarbamoyl.

6. A method according to claim 5 wherein the compound administered is 1-(2,6-difluorophenyl)methyl-1H-1,2,3-triazole-4-carboxamide.

7. A method according to claim 5 wherein the attention disorder is attention deficit hyperactivity disorder.

8. A method according to claim 7 wherein the compound administered is 1-(2,6-difluorophenyl)methyl-1H-1,2,3-triazole-4-carboxamide.

* * * * *